United States Patent [19]

Wehner et al.

[11] 4,374,145
[45] Feb. 15, 1983

[54] TIN COMPOUNDS

[75] Inventors: Wolfgang Wehner, Zwingenberg, Fed. Rep. of Germany; Saleem Farooq, Ettingen, Switzerland; Hans-Günter Köstler, Heppenheim, Fed. Rep. of Germany

[73] Assignee: Ciba-Geigy Corporation, Ardsley, N.Y.

[21] Appl. No.: 301,570

[22] Filed: Sep. 14, 1981

[51] Int. Cl.³ .................... A01N 59/16; C07F 7/22
[52] U.S. Cl. ........................... 424/278; 424/288; 549/208; 260/429.7
[58] Field of Search ........... 260/429.7, 348.39, 348.44; 424/288, 278; 549/208

[56] References Cited

U.S. PATENT DOCUMENTS

| | | | |
|---|---|---|---|
| 2,749,213 | 6/1956 | Bruce | 424/131 |
| 3,070,615 | 12/1962 | Seyferth | 260/429.7 |
| 3,089,847 | 5/1963 | Thompson | 424/288 |
| 3,259,541 | 7/1966 | Schroder et al. | 260/429.7 |
| 3,264,177 | 8/1966 | Kenaga | 424/288 |
| 3,342,840 | 9/1967 | Sobolev | 260/348.44 |
| 3,344,019 | 9/1967 | Sowa | 107/22 |
| 3,389,048 | 6/1968 | Kenaga | 167/46 |
| 3,415,857 | 12/1968 | Hoye | 260/429.7 |
| 3,440,255 | 4/1969 | Matsuda | 260/429.7 |
| 3,445,249 | 5/1969 | Leebrick | 106/15 |
| 3,470,220 | 9/1969 | Moedritzer et al. | 260/429 |
| 3,661,911 | 5/1972 | Meyer | 260/429.7 |
| 3,789,057 | 1/1974 | Reifenberg et al. | 260/429.7 |
| 3,792,059 | 2/1974 | Hechenbleikner | 260/429.7 |
| 3,806,467 | 4/1974 | Watanabe et al. | 252/429 R |
| 4,221,811 | 9/1980 | Bulten | 260/429.7 |

Primary Examiner—Norma S. Milestone
Attorney, Agent, or Firm—Frederick H. Rabin

[57] ABSTRACT

The invention relates to organo-tin ammonium salts of the formula

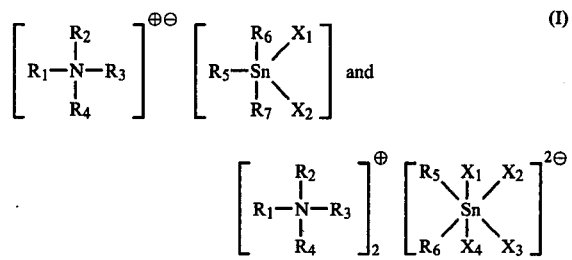

wherein each of $R_1$, $R_2$ and $R_3$ is hydrogen, alkyl, unsubstituted or acylated haloalkyl, halohydroxyalkyl, hydroxyalkyl, dihaloalkyl, or epoxyalkyl; $R_4$ is unsubstituted or acylated haloalkyl, halohydroxyalkyl, hydroxyalkyl, dihaloalkyl, epoxyalkyl or benzyl; $R_5$ is $C_1$–$C_6$-alkyl, cyclohexyl or phenyl; each of $R_6$ and $R_7$ is halogen, $C_1$–$C_6$-alkyl, cyclohexyl or phenyl; and each of $X_1$ to $X_4$ is halogen.

A process for the production of these compounds and their use in pest control are also described.

9 Claims, No Drawings

TIN COMPOUNDS

The present invention relates to organo-tin ammonium salts, to the production thereof and to the use thereof in pest control.

The organo-tin ammonium salts have the formulae

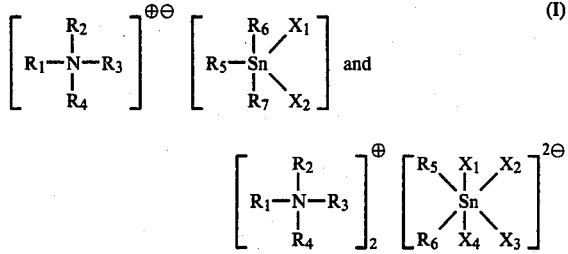

wherein each of $R_1$, $R_2$ and $R_3$ is hydrogen, alkyl, unsubstituted or acylated haloalkyl, halohydroxyalkyl, hydroxyalkyl, dihaloalkyl, or epoxyalkyl; $R_4$ is unsubstituted or acylated haloalkyl, halohydroxyalkyl, hydroxyalkyl, dihaloalkyl, epoxyalkyl or benzyl; $R_5$ is $C_1$-$C_6$-alkyl, cyclohexyl or phenyl; each of $R_6$ and $R_7$ is halogen, $C_1$-$C_6$-alkyl, cyclohexyl or phenyl; and each of $X_1$ to $X_4$ is halogen.

Halogen within the scope of the above definitions denotes fluorine, chlorine, bromine or iodine, with chlorine or bromine being preferred.

The alkyl, haloalkyl, halohydroxyalkyl, hydroxyalkyl, dihaloalkyl or epoxyalkyl groups within the definitions of $R_1$ to $R_7$ can be straight-chain or branched, and those groups defined by $R_1$ to $R_4$ contain preferably 1 to 20, most preferably 1 to 6, carbon atoms in the chain. Representative examples of such groups are: methyl, ethyl, ethyl chloride, ethyl bromide, propyl, isopropyl, n-butyl, isobutyl, sec- and tert-butyl, n-pentyl, n-hexyl, n-octyl, n-dodecyl, n-nonadecyl, n-eicosyl, and the isomers thereof, e.g. 2-ethylhexyl,

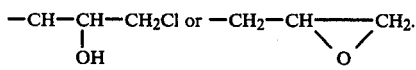

Preferred compounds of the formula I are those wherein each of $R_1$, $R_2$ and $R_3$ is methyl; $R_4$ is chloroethyl, bromoethyl, 3-chloro-2-hydroxypropyl, 2-hydroxyethyl or benzyl; $R_5$ is methyl, cyclohexyl or phenyl; each of $R_6$ and $R_7$ is chlorine, cyclohexyl or phenyl; $X_1$ is chlorine and $X_2$ is chlorine or bromine.

The most preferred compounds of the formula I, however, are those wherein each of $R_1$, $R_2$ and $R_3$ is methyl, $R_4$ is chloroethyl, bromoethyl, 3-chloro-2-hydroxypropyl, 2-hydroxyethyl or benzyl, each of $R_5$, $R_6$ and $R_7$ is cyclohexyl, $X_1$ is chlorine, and $X_2$ is chlorine or bromine.

The organo-tin ammonium salts of the formula I can be obtained by methods which are known per se, e.g. as follows:

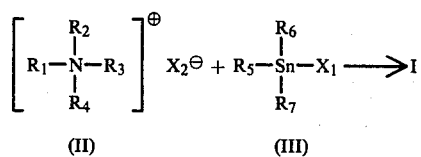

In the formulae II and III above, $R_1$ to $R_7$ and $X_1$ and $X_2$ are as defined for formula I.

The process is conveniently carried out in the temperature range from $-10°$ to $+180°$ C., preferably from $80°$ to $150°$ C., under normal or slightly elevated temperature, and preferably in the presence of a solvent or diluent which is inert to the reactants.

Examples of suitable solvents or diluents are: alcohols such as methanol, ethanol or isopropanol; ethers and ethereal compounds such as diethyl ether, dioxane and tetrahydrofurane; and ketones such as acetone, cyclohexanone or methyl ethyl ketone.

The starting materials of the formulae II and III are known and can be prepared by known methods.

The compounds of formula I are suitable for controlling a variety of pests of animals and plants and they also have a fungicidal and plant regulating action. Accordingly, they can be used for controlling insects, for example of the orders Lepidoptera, Coleoptera, Homoptera, Heteroptera, Diptera, Acarina, Thysanoptera, Orthoptera, Anoplura, Siphonaptera, Mallophaga, Thysanura, Isoptera, Psocoptera and Hymenoptera, and for controlling phytopathogenic mites and ticks of the order Acarina.

Of especial importance is the fact that the compounds of the formula I have a surprisingly potent and specific action against plant-destructive mites and mites which are parasites of animals. Thus the compounds of the formula I can be employed for controlling phytophagous mites e.g. of the families Tetranychidae and Phytoptipalpidae (spider mites), Tarsonemidae (soft-bodied mites) and Eriophyidae (gall mites). The compounds of formula I are suitable in particular for controlling the following species of mites which infest crops of fruit and vegetables: *Tetranychus urticae, Tetranychus cinnabarinus, Panonychus ulmi, Bryobia rubrioculus, Panonychus citri, Eriophyes pyri, Eriophyes ribis, Eriophyes vitis, Tarsomemus pallidus, Phyllocoptes vitis* and *Phyllocoptura oleivora*. With the aid of compounds of formula I it is also possible to control parasitic mites e.g. of the families Sarcoptidae, Psoroptidae, Dermanyssidae and Demodicidae, in particular scab mites of the species *Sarcoptes scabiei* and *Notoedres cati*, which penetrate deep into the epidermis as far as the nerve ends of domestic animals and productive livestock infested by them and caused severe irritation and damage, and also mites of the species *Dermanyssus gallinae* and *Psoroptes ovis*.

The compounds of the formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. The methods of application, such as spraying, atomising, dusting, scattering or pouring, are chosen in accordance with the intended objectives and the prevailing circumstances, just like the nature of the compositions.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyl-taurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylene-diaminopropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyoxyethylene adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ringwood, N.J., 1979.

The pesticidal formulations usually contain 0.1 to 99%, preferably 0.1 to 95%, of a compound of the formula I, 1 to 99.9% of a solid or liquid adjuvant, and 0 to 25%, preferably 0.1 to 25%, of a surfactant.

Whereas commercial products are preferably formulated as concentrates, the end user will normally employ dilute formulations.

The formulations can also contain further additives such as stabilisers, antifoams, viscosity regulators, binders, adhesives, as well as fertilisers, in order to produce special effects.

FORMULATION EXAMPLES

Formulation Examples for liquid active ingredients of the formula I (throughout, percentages are by weight)

| (1) Emulsifiable concentrates | (a) | (b) | (c) |
|---|---|---|---|
| active ingredient | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any required concentration can be produced from such concentrates by dilution with water.

| (2) Solutions | (a) | (b) | (c) | (d) |
|---|---|---|---|---|
| active ingredient | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| (3) | Granulates | (a) | (b) |
|---|---|---|---|
| | active ingredient | 5% | 10% |
| | kaolin | 94% | — |
| | highly dispersed silicic acid | 1% | — |
| | attapulgite | — | 90% |

The active ingredient is dissolved in methylene chloride, the solution is sprayed onto the carrier, and the solvent is subsequently evaporated off in vacuo.

| (4) | Dusts | (a) | (b) |
|---|---|---|---|
| | active ingredient | 2% | 5% |
| | highly dispersed silicic acid | 1% | 5% |
| | talcum | 97% | — |
| | kaolin | — | 90% |

Ready-for-use dusts are obtained by intimately mixing the carriers with the active ingredient.

Formulation examples for solid active ingredients of the formula I (throughout, percentages are by weight)

| (5) Wettable powders | (a) | (b) |
|---|---|---|
| active ingredient | 20% | 60% |
| sodium lignosulfonate | 5% | 5% |
| sodium laurylsulfate | 3% | — |
| sodium diisobutylnaphthalenesulfonate | — | 6% |
| octylphenol polyethylene glycol ether (7–8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable poweders which can be diluted with water to give suspensions of the desired concentration.

| (6) | Emulsifiable concentrate | |
|---|---|---|
| | active ingredient | 10% |
| | octylphenol polyethylene glycol ether (4–5 moles of ethylene oxide) | 3% |
| | calcium dodecylbenzenesulfonate | 3% |
| | castor oil polyglycol ether (36 moles of ethylene oxide) | 4% |
| | cyclohexanone | 30% |
| | xylene mixture | 50% |

Emulsions of any required concentration can be obtained from this concentrate by dilution with water.

| (7) | Dusts | (a) | (b) |
|---|---|---|---|
| | active ingredient | 5% | 8% |
| | talcum | 95% | — |
| | kaolin | — | 92% |

Dusts which are ready for use are obtained by mixing the active ingredient with the carriers, and grinding the mixture in a suitable mill.

| (8) | Extruder granulate | |
|---|---|---|
| | active ingredient | 10% |
| | sodium lignosulfonate | 2% |
| | carboxymethylcellulose | 1% |
| | kaolin | 87% |

The active ingredient is mixed and ground with the adjuvants, and the mixture is subsequently moistened with water. The mixture is extruded and then dried in a stream of air.

| (9) | Coated granulate | |
|---|---|---|
| | active ingredient | 3% |
| | polyethylene glycol 200 | 3% |
| | kaolin | 94% |

The finely ground active ingredient is uniformly applied, in a mixer, to the kaolin moistened with polyethylene glycol. Non-dusty coated granulates are obtained in this manner.

| (10) | Suspension concentrate | |
|---|---|---|
| | active ingredient | 40% |
| | ethylene glycol | 10% |
| | nonylphenol polyethylene glycol ether (15 moles of ethylene oxide) | 6% |
| | sodium lignosulfonate | 10% |
| | carboxymethylcellulose | 1% |
| | 37% aqueous formaldehyde solution | 0.2% |
| | silicone oil in the form of a 75% aqueous emulsion | 0.8% |
| | water | 32% |

The finely ground active ingredient is intimately mixed with the adjuvants, giving a suspension concentrate from which suspensions of any desired concentration can be obtained by dilution with water.

EXAMPLE 1

Preparation of the salt of the formula

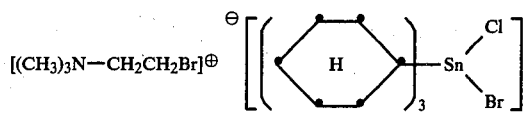

80.7 g of the compound of the formula

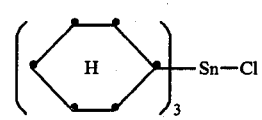

and 49.4 g of the salt of the formula $(CH_3)_3 \oplus N—CH_2CH_2Br \ Br \ominus$ are dissolved in a mixture of 300 ml of methanol and 550 ml of acetone. The solution is heated under reflux for 1 hour and concentrated. Precipitation with diethyl ether yields the compound of the formula

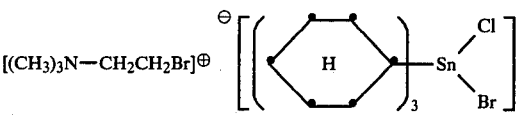

with a melting point of 205°–210° C.
The following compounds are also prepared in analogous manner:
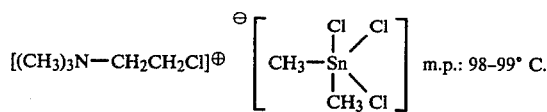 m.p.: 98–99° C.
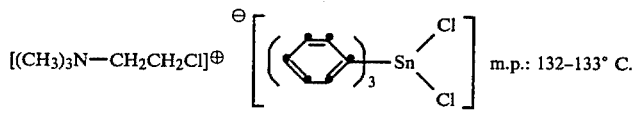 m.p.: 132–133° C.
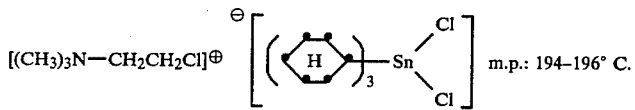 m.p.: 194–196° C.
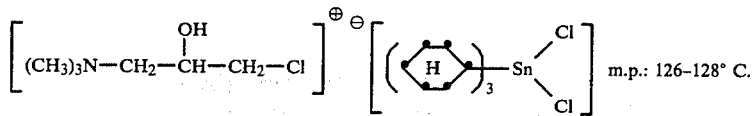 m.p.: 126–128° C.
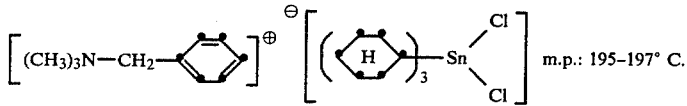 m.p.: 195–197° C.
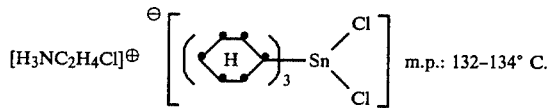 m.p.: 132–134° C.
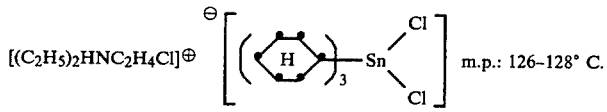 m.p.: 126–128° C.
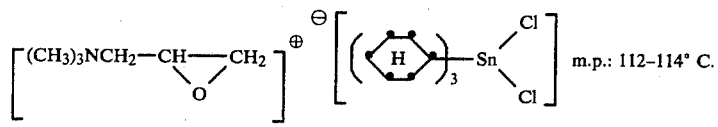 m.p.: 112–114° C.
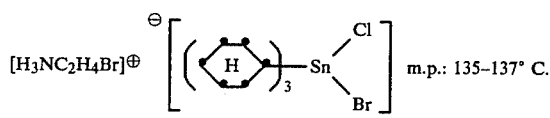 m.p.: 135–137° C.
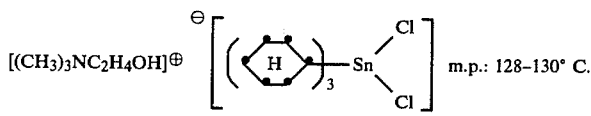 m.p.: 128–130° C.
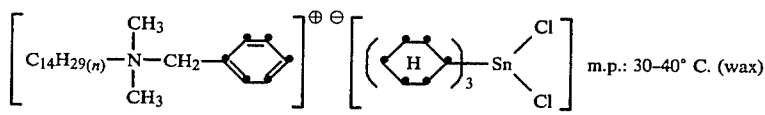 m.p.: 30–40° C. (wax)
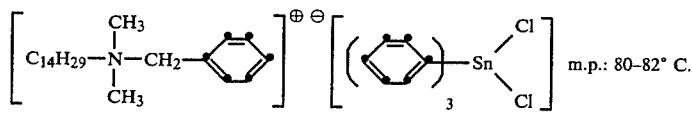 m.p.: 80–82° C.

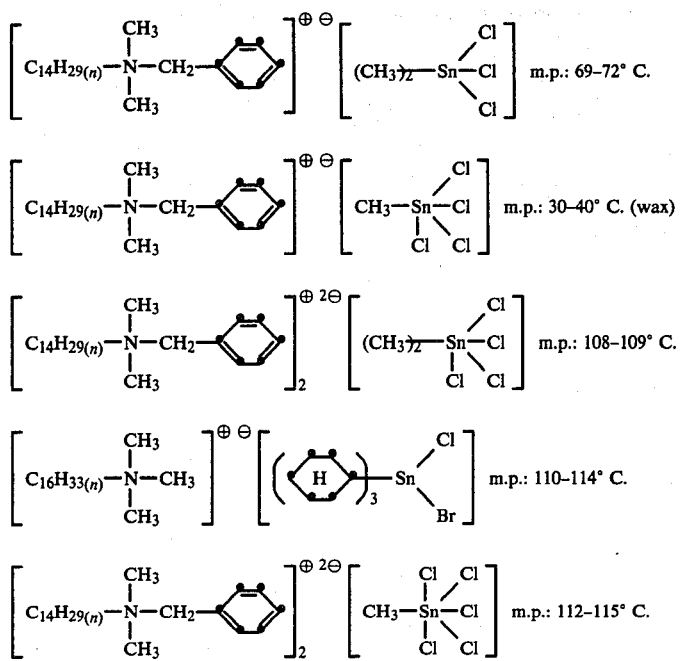

EXAMPLE 2

Action against plant-destructive acarids: *Tetranychus urticae* (OP-sensitive) and *Tetranychus cinnabarinus* (OP-tolerant)

16 hours before the test for acaricidal action, the primary leaves of Phaseolus vulgaris plants are infected with an infested piece of leaf from a mass culture of *Tetranychus urticae* (OP-sensitive) or *Tetranychus cinnabarinus* (OP-tolerant). (The tolerance refers to the tolerance to diazinone). The treated, infested plants are sprayed dripping wet with a test solution containing 25, 50, 100 or 200 ppm of the compound to be tested. A count of the number of living and dead imagines and larvae (all mobile stages) is made under a stereoscopic microscope after 24 hours and again after 7 days. One plant is used for each test substance and test species. During the test run, the plants are kept in greenhouse compartments at 25° C.

Within the above indicated concentration limits, the compounds of the preparatory Examples are effective against larvae of the species *Tetranychus urticae* and *Tetranychus cinnabarinus* (vide the following table).

Biological test results

The results of the test carried out in the foregoing Example are reported in the table, using the following rating to indicate the percentage kill of the pests:

A: 100% kill at a concentration of 25 ppm
B: 100% kill at a concentration of 50 ppm
C: 100% kill at a concentration of 100 ppm
D: 100% kill at a concentration of 200 ppm.

| Compounds | Activity Tetranychus urticae Larvae | Tetranychus cinnabarinus Larvae |
|---|---|---|
| $[(CH_3)_3N-CH_2CH_2Br]^{\oplus\ominus}$ $[(C_5H_5)_3Sn(Cl)(Br)]$ | B | A |
| $[(CH_3)_3N-CH_2CH_2Cl]^{\oplus\ominus}$ $[CH_3-Sn(Cl)_2(CH_3)(Cl)]$ | C | B |
| $[(CH_3)_3N-CH_2CH_2Cl]^{\oplus\ominus}$ $[(C_5H_5)_3Sn Cl_2]$ | C | B |
| $[(CH_3)_3N-CH_2CH_2Cl]^{\oplus\ominus}$ $[(C_5H_5)_3Sn Cl_2]$ | C | B |

-continued

| Compounds | Activity Tetranychus urticae Larvae | Tetranychus cinnabarinus Larvae |
|---|---|---|
| [H₃NC₂H₄Cl]⁺⁻ [(C₆H₅)₃Sn(Cl)Cl]⁻ | C | — |
| [(CH₃)₃N—CH₂—C₄H₃]⁺⁻ [(C₆H₅)₃Sn(Cl)Cl]⁻ | B | A |
| [(CH₃)₃N—CH₂—CH(OH)—CH₂—Cl]⁺⁻ [(C₆H₅)₃Sn(Cl)Cl]⁻ | B | A |
| [(C₂H₅)₂HNC₂H₄Cl]⁺⁻ [(C₆H₅)₃Sn(Cl)Cl]⁻ | C | — |
| [(CH₃)₃NCH₂—CH(O)CH₂]⁺⁻ [(C₆H₅)₃Sn(Cl)Cl]⁻ | C | — |
| [H₃NC₂H₄Br]⁺⁻ [(C₆H₅)₃Sn(Cl)Br]⁻ | C | — |
| [(CH₃)₃NC₂H₄OH]⁺⁻ [(C₆H₅)₃Sn(Cl)Cl]⁻ | C | — |
| [C₁₄H₂₉(n)—N(CH₃)₂—CH₂—C₄H₃]⁺⁻ [(C₆H₅)₃Sn(Cl)Cl]⁻ | C | B |
| [C₁₄H₂₉—N(CH₃)₂—CH₂—C₄H₃]⁺⁻ [(C₆H₅)₃Sn(Cl)Cl]⁻ | C | B |

What is claimed is:
1. An organo-tin substituted ammonium salt of the formula:

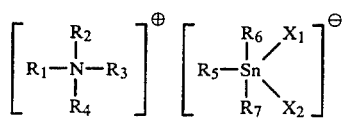

or of the formula:

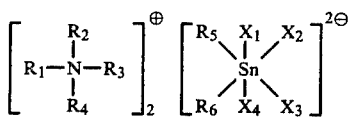

wherein each of $R_1$, $R_2$, and $R_3$ is hydrogen or the same or different alkyl of up to 20 carbon atoms;
$R_4$ is epoxyalkyl, haloalkyl or halohydroxyalkyl, each containing up to 6 carbon atoms;
$R_5$ is alkyl of up to 6 carbon atoms, cyclohexyl or phenyl;

each of $R_6$ and $R_7$, independently of the other, is either the same as $R_5$ or the same as $X_1$ as hereinafter defined;

$X_1$ is chloro or bromo; and $X_2$, $X_3$ and $X_4$ are either all chloro or all bromo.

2. The compound according to claim 1 of the formula

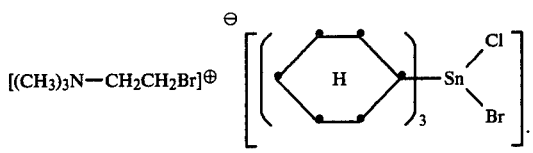

3. The compound according to claim 1 of the formula

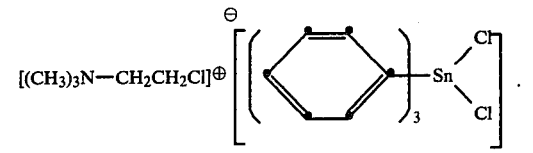

4. The compound according to claim 1 of the formula

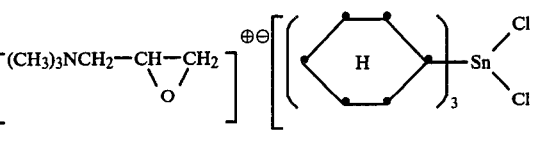

5. A compound according to claim 1 wherein said organo-tin substituted ammonium salt is of the formula:

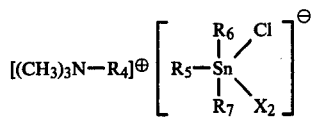

wherein $R_4$ is chloroethyl, bromoethyl or 3-chloro-2-hydroxypropyl;

$R_5$ is methyl, cyclohexyl or phenyl;

each of $R_6$ and $R_7$, independently of the other, is chloro, cyclohexyl or phenyl; and $X_2$ is chloro or bromo.

6. A compound according to claim 5 wherein each of $R_5$, $R_6$ and $R_7$ is cyclohexyl.

7. A compound according to claim 5 wherein said organo-tin substituted ammonium salt is of the formula:

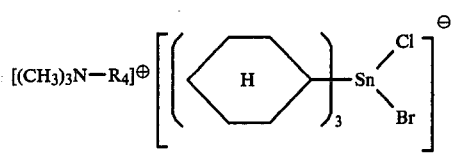

wherein $R_4$ is as therein defined.

8. A pesticidal composition comprising an effective amount of a compound according to claim 1 and a carrier therefor.

9. A method of controlling animal and plant pests which comprises applying a pesticidally effective amount of a compound according to claim 1 to the locus of said pests.

* * * * *